United States Patent [19]

Deluca et al.

[11] Patent Number: 4,970,203

[45] Date of Patent: Nov. 13, 1990

[54] METHOD FOR IMPROVING REPRODUCTIVE FUNCTIONS IN MAMMALS

[76] Inventors: Hector F. Deluca, 1809 Hwy. BB, Deerfield, Wis. 53531; Gary G. Kwiecinski, 907 Tall Trees Dr., Scranton, Pa. 18505

[21] Appl. No.: 281,993

[22] Filed: Dec. 9, 1988

[51] Int. Cl.$^5$ ............................................. A61K 31/59
[52] U.S. Cl. .................................................. 514/167
[58] Field of Search ......................................... 514/167

[56] References Cited

PUBLICATIONS

Chemical Abstracts 93(13):131074v "Effect of Vitamin D Deficiency on Fertility and Reproductive Capacity in the Female Rat" 1980.

"Effect of Vitamin D Deficiency on Fertility and Reproductive Capacity in the Female Rat", Bernard P. Halloran et al., Journal of Nutrition, vol. 110, No. 8, Aug. 1980, pp. 1573–1580.

"Is 1,25-Dihydroxyvitamin D Required for Reproduction?", Bernard P. Halloran, Society for Experimental Biology and Medicine, vol. 191, 1989, pp. 227–232.

"Vitamin A and Reproduction in Rats", J. N. Thompson et al., Proceedings of the Royal Society, (1964), pp. 510–535.

"Differences in Testis Injury and Repair After Vitamin A-Deficiency, Vitamin E-Deficiency, and Inanition", Karl E. Mason, The American Journal of Anatomy, vol. 52, No. 2, Mar., 1933, pp. 153–239.

*Primary Examiner*—Douglas W. Robinson
*Assistant Examiner*—Raymond J. Henley, III
*Attorney, Agent, or Firm*—Andrus, Sceales, Starke & Sawall

[57] ABSTRACT

A method of improving the fertility and reproductive capacity of male and female mammals by administering an amount of a vitamin D compound, such as vitamin $D_3$, its active form 1,25-dihydroxyvitamin $D_3$ or other compounds exhibiting vitamin D-like activity, to the mammal.

16 Claims, No Drawings

METHOD FOR IMPROVING REPRODUCTIVE FUNCTIONS IN MAMMALS

TECHNICAL FIELD

The present invention relates to reproductive functions in mammals, and more particularly to a method for improving reproductive functions in mammals by the administration of a vitamin D compound, such as vitamin $D_3$, its active form 1,25-dihydroxyvitamin $D_3$ or other compounds exhibiting vitamin D-like activity, to the mammal.

BACKGROUND AND SUMMARY OF THE INVENTION

Although vitamin D is clearly essential for the regulation of calcium (Ca) and $P_i$ metabolism, its role in reproduction is poorly defined, especially in mammals. During pregnancy and lactation, the rate of synthesis and plasma levels of 1,25-dihydroxyvitamin $D_3$ (1,25-$(OH)_2D_3$), the hormonally active form of vitamin D, are increased. Although vitamin D-deficient female rats can reproduce, it is known that the absence of vitamin D diminishes their mating success and fertility as well as litter size and neonatal growth. Thus, vitamin D appears to play a role in female reproduction. However, to date, no attempt has been made to determine if vitamin D is required for reproductive functions of the male. This is particularly important since the receptor for 1,25-$(OH)_2D_3$ has been found in male reproductive organs.

Thus, in accordance with the present disclosure, it has been found that although vitamin D-deficient male mammals can reproduce, vitamin D deficiency in male mammals markedly reduces their mating success and fertility. Additionally, it has been found that diminished reproductive functions of male and female mammals may be improved dramatically by the administration of vitamin D compounds such as vitamin $D_3$ and 1,25-$(OH)_2D_3$, as well as by other compounds having vitamin D-like activity.

Disclosure of the Invention

The present invention comprises a method for improving reproductive functions in a mammal which comprises administering to the mammal an amount of a vitamin D compound sufficient to improve fertility and reproductive capacity of the mammal.

As used herein the term "vitamin D compound" encompasses compounds which control one or more of the various vitamin D-responsive processes in mammals, i.e. intestinal calcium absorption, bone mobilization, bone mineralization, and cell differentiation. Thus the vitamin D compounds encompassed by this invention include cholecalciferol and ergocalciferol and their known metabolites, as well as the known synthetic cholecalciferol and ergocalciferol analogs which express calcemic or cell differentiation activity. These synthetic cholecalciferol and ergocalciferol analogs comprise such categories of compounds as the 5,6-trans-cholecalciferols and 5,6-trans-ergocalciferols, the fluorinatriol cholecalciferols, the side chain homologated cholecalciferols and side chain homologated $\Delta^{22}$-cholecalciferols, the side chain-truncated cholecalciferols, and the 10,19-dihydrovitamin D compounds. Specific examples of such compounds include vitamin D metabolites or analogs such as vitamin $D_3$, vitamin $D_2$, $1\alpha$-hydroxyvitamin $D_3$, $1\alpha$-hydroxyvitamin $D_2$ $1\alpha,25$-dihydroxyvitamin $D_3$, $1\alpha 25$-dihydroxyvitamin $D_2$, $1\alpha,25$-hydroxyvitamin $D_3$, $1\alpha 25$-hydroxyvitamin $D_2$, 24,24-difluoro-25-hydroxyvitamin $D_3$, 24,24-difluoro-1$\alpha$25-dihydroxyvitamin $D_3$, 24-fluoro-25-hydroxyvitamin $D_3$, 24-fluoro-1$\alpha$,25-dihydroxyvitamin $D_3$, 2$\beta$-fluoro-25-hydroxyvitamin $D_3$, 2$\beta$-fluoro-1$\alpha$-hydroxyvitamin $D_3$ 2$\beta$-fluoro-1$\alpha$,25-dihydroxyvitamin $D_3$, 26,26,26,27,27,27-hexafluoro-25-hydroxyvitamin $D_3$, 26,26,26,27,27,27-hexafluoro-1o,25-dihydroxyvitamin $D_3$, 24,25-dihydroxyvitamin $D_3$ 1$\alpha$24,24-trihydroxyvitamin $D_3$, 25,26-dihydroxyvitamin $D_3$, 1$\alpha$25,26-trihydroxy-vitamin $D_3$, 23,25-dihydroxyvitamin $D_3$, 23,25,26-trihydroxyvitamin $D_3$, and the corresponding 1$\alpha$-hydroxylated forms, 25-hydroxyvitamin $D_3$-26,23-lactone and its 1$\alpha$-hydroxylated derivative, the side chain nor, dinor, trinor and tetranor-analogs of 25-hydroxyvitamin $D_3$ and of 1$\alpha$,25-dihydroxyvitamin $D_3$, 1$\alpha$-hydroxypregnacalciferol, and its homo and dihomo derivatives, 1$\alpha$,25-dihydroxy-24-epi-vitamin $D_2$, 24-homo-1,25-dihydroxyvitamin $D_3$ 24-dihomo-1,25-dihydroxyvitamin $D_3$ 24-trihomo-1,25-dihydroxyvitamin $D_3$ and the corresponding 26- or 26,27-homo, dihomo or trihomo analogs of 1o,25-dihydroxyvitamin $D_3$.

The vitamin D compounds or combinations thereof with other vitamin D derivatives or other therapeutic agents, can be readily administered as sterile parenteral solutions by injection or intravenously, or by alimentary canal in the form of oral dosages, or trans-dermally, or by suppository. Doses of from about 0.1 micrograms to about 2 milligrams per day of a vitamin D compound per se, or in combination with other vitamin D derivatives, for a period of about 1 week to about 8 months, the proportions of each of the compounds in the combination being dependent upon the particular mammal being treated and the degree of improvement desired, are generally effective to practice the present invention. Although the actual amount of the vitamin D compound used is not critical, in all cases sufficient amount of the compound should be used to improve fertility and reproductive capacity of the mammal. Amounts in excess of about 2 milligrams per day of the vitamin D compound, above, or the combination of that compound with vitamin D derivatives, are generally unnecessary to achieve the desired results and may not be economically sound practice. In practice, it is understood that the specific dosage administered in any given case will be adjusted in accordance with the specific compounds being administered, the mammal to be treated, the condition of the subject and the other relevant medical facts that may modify the activity of the drug or the response of the subject, as is well known by those skilled in the art.

Dosage forms of the various compounds can be prepared by combining them with non-toxic pharmaceutically acceptable carriers as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The present invention is further described by means of the following illustrative examples.

EXAMPLE I

Male and female age-matched, Sprague Dawley rats (Harlan Sprague Dawley, Madison, Wis.) were obtained as weanlings and divided into groups. All vitamin D-deficient rats were maintained on a purified diet containing 0.47% Ca and 0.3% $P_i$. One-half of the vitamin D-replete males and females were maintained on the same diet as the vitamin D-deficient males but received 2 μg of vitamin $D_3$ (cholecalciferol) per week in 0.1 ml of propylene glycol by a single intraperitoneal injection. The other half of the vitamin D-replete males and females were maintained on a standard laboratory rodent ration (Wayne Rodent Blox, Continental Grain Co., Chicago, Ill.). All animals were maintained on a light cycle of 14 hours light and 10 hours dark. Light in the vitamin D-deficient room was provided by incandescent lighting and all potential sources of ultraviolet light were eliminated to exclude the possibility of endogenous vitamin D production by the skin.

At approximately 90 days of age, females were confirmed sexually mature by daily vaginal smears. They were mated at 90 and again at 170 days of age. The mating procedure involved placing 1 or 2 vitamin D-replete females with one vitamin D-deficient or one vitamin D-replete male. The animals were left together until the females became pregnant or for a maximum period of 10 days. Vaginal smears were taken each morning and scored as to the day of the estrous cycle and as to whether or not sperm were present. A sperm-positive smear was taken as evidence of a successful mating and used to establish the first day of pregnancy. Successfully mated females were moved to individual maternity cages having a solid bottom and carpeted with wood shavings. Pregnant animals were observed daily, and at parturition the number of pups per litter was recorded.

A preliminary analysis of the data indicated that vitamin D deficiency in male rats significantly reduced mating success and fertility in vitamin D-replete female rats. To determine if impaired reproductive function of vitamin D-deficient male rats was reversible, the vitamin D-deficient males were divided into two groups after mating to vitamin D-replete females and given vitamin D. One group received 100 ng of 1,25-$(OH)_2D_3$ per day in 0.1 ml propylene glycol by a single intraperitoneal injection. The other group received 2 μg of vitamin $D_3$ (cholecalciferol) per week in 0.1 ml of propylene gylcol by a single injection. Vitamin D replacement was provided for 3 weeks prior to and throughout their second matings to vitamin D-replete females.

Random blood samples were obtained by tail bleedings from animals prior to mating for the first time, after mating for the first time (immediately prior to vitamin D replacement), and prior to their second mating (three weeks after the beginning of vitamin D replacement). Serum samples were assayed for total Ca and $P_i$ Serum Ca concentrations were determined by combining 0.1 ml of serum with 1.9 ml of 0.1% $LaCl_3$ and measuring Ca concentration by atomic absorption spectroscopy (Model 403, Perkin-Elmer Corp., Norwalk, Conn.). Serum $P_i$ concentrations were determined colorimetrically on 10 μl of serum.

To confirm that vitamin D-deficient animals were deficient, random serum samples were obtained by exsanguination from males and females at the end of their first mating (immediately prior to the administration of vitamin D treatment to the remaining vitamin D-deficient animals). These samples were analyzed for 25-hydroxyvitamin $D_3$ (25-OH-$D_3$) and 1,25$(OH)_2D_3$ by established methods.

Data are expressed as the mean ± standard deviation of the mean. The statistical significance was determined by a comparison of proportions and the Student's two-tailed t-test using 95% confidence intervals.

Upon preliminary analysis of the data, no differences were found in values obtained between vitamin D-replete animals fed the vitamin D-deficient diet with vitamin D supplementation by intraperitoneal injection and vitamin D-replete animals fed the standard laboratory rodent ration. Therefore, all data for vitamin D-replete animals from both diet groups were combined for subsequent analysis and presentation.

Serum Ca and $P_i$ concentrations of vitamin D-replete and vitamin D-deficient animals are given in Table 1. Serum Ca concentrations were significantly lower in vitamin D-deficient males but serum $P_i$ concentrations were unaffected by vitamin D deficiency. Vitamin D-deficient males prior to mating for the first time had a significantly lower serum Ca concentration (5.1±0.5/100 ml) when compared to serum Ca concentrations from vitamin D-replete males (9.9± 0.5 mg/100 ml). Postmating, pre-treatment, vitamin D-deficient males had a significantly lower serum Ca concentration (7.1±0.6 mg/ml) than vitamin D-replete males (10.0±0.2 mg/ml). For vitamin D-deficient males, the post-mating serum Ca concentration increased when compared to the values obtained prior to mating in the same animals. For vitamin D-deficient male rats that received vitamin $D_3$ or 1,25-$(OH)_2D_3$ treatment, serum Ca and $P_i$ concentrations were not different from values of vitamin D-replete male rats.

Serum from vitamin D-replete males contained 9±2 ng/ml of 25-OH-$D_3$ and 29±8 pg/ml of 1,25-$(OH)_2D_3$, while serum from vitamin D-replete females contained 12±2 ng/ml of 25-OH-$D_3$ and 54±14 pg/ml of 1,25-$(OH)_2D_3$. Vitamin D-deficient male serum had significantly lower levels of 25-OH-$D_3$ non-detectable) and 1,25-$(OH)_2D_3$ (10±4 pg/ml). With respect to 25-OH-$D_3$, these results verify that the animals fed the vitamin D-deficient diet were, in fact, vitamin D-deficient. However, because of the finite detectability limits for the 1,25-$(OH)_2D_3$ assay (lower limit of detectability is 10 pg/ml), it is apparent that these animals were vitamin D deficient.

The overall effects of vitamin D deficiency in male rats on mating and fertility) are summarized in Table 2. In order to quantitate fertility, two known ratios were applied (See Halloran, B. P. and H. F. DeLuca (1980) Effect of vitamin D deficiency on fertility and reproductive capacity in the female rat. J. Nutr. 110:1573–1580), i.e. the mating ratio and the fertility ratio. The mating ratio is the total number of females becoming pregnant (sperm-positive smears) divided by the total animal days mated (the summation number of animals times the number of days each female was exposed to a male). The fertility ratio is defined as the total number of females becoming pregnant and giving birth to normal, healthy litters divided by the total animal days mated. Normal, healthy litters were born to females that demonstrated no complications during pregnancy and parturition.

The mating ratio attempts to measure the likelihood of a successful mating and assuming an estrus cycle of 4-5 days, the theoretical value should be 0.20-0.25. From Table 2, the observed mating ratio value of vitamin D-replete animals was 0.20, in agreement with the theoretical value. For vitamin D-deficient animals, the mating ratio was 0.11, implying that the likelihood of a successful mating in the vitamin D-deficient state was approximately 55% that in the vitamin D-replete state. The number of males successfully inseminating females was 73% of the total number of animals mated in the vitamin D-deficient state. This was significantly different from the number of vitamin D-replete males inseminating females, where 90% of the total number of vitamin D-replete males successfully mated.

The fertility ratio provides a means of quantitating the likelihood of a successful mating and pregnancy. The fertility ratio would equal the mating ratio if every mating resulted in the delivery of normal, healthy litters. For matings from vitamin D-replete males (Table 2), the fertility ratio was slightly less than the mating ratio, indicating that there were a few abnormal pregnancies and deliveries. In matings from vitamin D-deficient males, the fertility ratio was 0.04. This was significantly less than the mating ratio of 0.15 from vitamin D-replete males and indicates that the likelihood of a vitamin D-deficient male insemination giving rise to a pregnancy resulting in a normal, healthy litter was approximately 27% that observed in litters from females inseminated by vitamin D-replete males. These results show that the overall fertility in vitamin D-replete females inseminated by vitamin D-deficient males was reduced approximately 73% when compared to fertility in vitamin D-replete females inseminated by vitamin D-replete males.

Normal, healthy litters were litters born to females that demonstrated no complications during pregnancy and parturition. Complications encountered during pregnancy and parturition which resulted in diminished fertility include fetal resorption and pseudopregnancy, abortions, mothers dying giving birth and mothers giving birth to dead pups. The effect of vitamin D deficiency on the percentage of pregnant animals giving birth to normal, healthy litters are shown in Table 2. The percentage of pregnant animals giving birth to normal, healthy litters from vitamin D-deficient male inseminations was 40%. This was significantly different from the percentage of normal, healthy litters (76%) from pregnancies resulting by inseminations from vitamin D-replete males.

The effects of vitamin D treatment of mating and fertility in vitamin D-deficient male rats are summarized in Table 2. For matings from vitamin D-replete male rats, the mating ratio was 0.20 in agreement with the theoretical value of 0.20-0.25. For vitamin D-deficient males that received vitamin $D_3$ the mating ratio was 0.24 and for vitamin D-deficient males the received 1,25-$(OH)_2D_3$, the mating ratio was 0.22, both in agreement with the theoretical value and not different from vitamin D-replete male rats. The number of vitamin D-replete males that successfully mated with females was 87% of the total number mated. Vitamin D-deficient males repleted with vitamin $D_3$ were 94% successful at mating, while those receiving 1,25-$(OH)_2D_3$ were 100% effective. Thus, there were no significant differences in successful matings between the vitamin D-replete males and the vitamin D-deficient males that were administered the two forms of vitamin D.

The fertility ratio of vitamin D-deficient males that received vitamin $D_3$ was 0.12 and for vitamin D-deficient males that received 1,25-$(OH)_2D_3$, the fertility ratio was 0.07, both not significantly different from the fertility ratio of 0.11 of vitamin D-replete males. The fertility ratio of 0.11 in vitamin D-replete male rats was not different from the fertility ratio of 0.15 from the same animals when mated for the first time (Table 2).

As a result, it is concluded that although vitamin D-deficient male rats can reproduce an examination of their reproductive functions has shown that absence of vitamin D reduces fertility and reproductive capacity.

In this Example, serum concentrations of 1,25-$(OH)_2D_3$ in vitamin D-deficient males was found to be $10\pm4$ pg/ml. Although this value is significantly lower than the serum concentrations of 1,25-$(OH)_2D_3$ in vitamin D-replete animals and tests the limits of detectability of the 1,25-$(OH)_2D_3$ assay, it seems likely that these animals were not absolutely vitamin D deficient. At the time blood was drawn for serum vitamin D determinations, serum Ca concentrations in vitamin D-deficient males had risen to $7.1\pm0.6$ mg/100 ml from $5.1\pm0.5$ mg/100 ml prior to mating. It is possible that this increase is due to contamination by vitamin D. Since vitamin D-deficient males were housed in the same cages with vitamin D-replete females for up to 10 days while mating, there is the possibility of transfer of vitamin D (e.g. coprophagy, grooming). However, with serum concentrations of 1,25-$(OH)_2D_3$ on the order of $10\pm4$ /ml, nondetectable levels of serum 25-OH-$D_3$, and serum Ca concentrations on the order of 5.1 mg/100 ml, it is evident that these animals were, in fact, severely vitamin D deficient.

The probability of a female becoming pregnant by a vitamin D-deficient male rat in a given time period was approximately 55% that observed in vitamin D-replete male rats. The reason for this was not apparent as analysis of the daily vaginal smears taken showed that the females were in fact cycling in the normal 4-5 day period. Examination of the mating data showed that the number of males in the vitamin D-deficient state that inseminated females was 73% of the total number of mated, vitamin D-deficient males. This was significantly different from vitamin D-replete male rats, were 90% of the total number of mated, vitamin D-replete male rats inseminated females.

The probability of vitamin D-deficient male inseminations giving rise to normal healthy litters in vitamin D-replete females was 40% of the total number of pregnancies. This was significantly different from vitamin D-replete male inseminations which gave rise to normal, healthy litters in 76% of the pregnancies induced in vitamin D-replete females. The reason for this difference is primarily due to the developement of a greater number of complications during pregnancy that resulted in abnormal litters. It has been suggested that the reduction in fertility and litter size in vitamin D-deficient female rats may not be directly influenced by vitamin D deficiency, but rather a result of the fact that vitamin D-deficient females were smaller in size. In this Example, vitamin D-replete females maintaining a successful pregnancy and parturition were similar for both vitamin D-deficient and vitamin D-replete male inseminations. No significant differences were found in litter sizes from both groups of inseminations, although there was a tendency toward smaller litter sizes in the vitamin D-deficient male inseminated females. These observations suggest the increased probability of complications during pregnancy and parturition and the reduction in litter sizes were influenced directly by vitamin D status of the male since the vitamin D-replete females were the same.

The most important finding is that vitamin $D_3$ is able to improve or restore reproductive capacity in male rats within three weeks. Thus, deficiency of vitamin D does not produce irreversible sterility unlike vitamin A deficiency. Also it is interesting to note that 1,25-$(OH)_2D_3$ is capable of restoring these reproductive functions, supporting the idea that 1,25-$(OH)_2D_3$ is probably the active form of vitamin D in the male reproductive functions. These results also support the idea that vitamin D is directly involved in these functions.

EXAMPLE II

Male and female age-matched, Sprague Dawley rats (Harlan Sprague Dawley, Madison, WI) were obtained as weanlings and divided into groups. Vitamin D-deficient females were divided into three groups. Group 1 vitamin D-deficient females were maintained on a purified diet containing 0.47% Ca and 0.3% $P_i$. Group 2 vitamin D-deficient females were maintained on a diet containing 1.2% Ca and 0.1% $P_i$. Group 3 vitamin D-containing deficient females were maintained on a diet containing 0.94% Ca and 0.3% $P_i$ until 1 week before mating when they were switched to and maintained on the same diet as Group 2 vitamin D-deficient females. One-half of the male and female vitamin D-replete animals were maintained on the same diet as Group 1 females but received 2 µg of vitamin $D_3$ (cholecalciferol) per week in 0.1 ml propylene glycol by a single intraperitoneal injection. The other half of the vitamin D-replete males and females were maintained on a standard laboratory rodent ration (Wayne Rodent Blox, Continental Grain Co., Chicago, Ill.). Animals were housed in hanging wire cages and maintained on a light cycle of 14 hours light, 10 hours dark. Light in the vitamin D-deficient room was provided by incandescent lighting and all potential sources of ultraviolet light were eliminated to exclude the possibility of endogenous vitamin D production by the skin.

At approximately 90 days of age, females were confirmed sexually mature by daily vaginal smears and mated. These animals were mated at 90 days and again at 170 days, after vitamin D-deficient females received vitamin D treatment. The mating procedure involved placing one to three vitamin D-replete or vitamin D-deficient females with one vitamin D-replete male. The animals were left together until females became pregnant or for a maximum period of 10 days. Vaginal smears were taken each morning and scored as to the day of the estrous cycle and as to whether or not sperm were present. A sperm-positive smear was taken as an indication of a successful mating and used to establish the first day of pregnancy. Successfully mated females were moved to individual maternity cages having a solid bottom and carpeted with wood shavings. Pregnant animals were observed daily for abortions and at parturition the number of pups per litter was recorded.

To determine if impaired reproductive functions in vitamin D-deficient female rats is reversible, Group 1 vitamin D-deficient females were divided into two groups after mating to vitamin D-replete males for the first time and administered vitamin D treatment. One group received 100 ng of 1,25-dihydroxyvitamin $D_3$ (1,25-$(OH)_2D_3$) per day in 0.1 ml propylene glycol by intraperitoneal injection. The second vitamin D treatment group received 2 µg and vitamin $D_3$ (cholecalciferol) per week in 0.1 ml of propylene glycol by intraperitoneal injection. Treatment was provided for three weeks prior to mating and throughout their second mating to vitamin D-replete males and throughout gestation until parturition.

Random samples of blood were obtained by tail bleeding from animals prior to mating for the first time, after mating for the first time (immediately prior to vitamin D treatment), and prior to their second mating (three weeks after the beginning of administration of vitamin D treatment). Serum samples were assayed for total Ca and $P_i$. Serum Ca concentrations were determined by combining 0.1 ml of serum with 1.9 ml of 0.1% $LaCl_3$ and measuring Ca concentration by atomic absorption spectroscopy (Model 403, Perkin-Elmer Corp., Norwalk, Conn.). Serum concentrations of $P_i$ were determined colorimetrically with 10 µl of serum.

To confirm that vitamin D-deficient animals were, in fact, deficient, random serum samples were obtained by exsanguination from males and females at the end of their first mating (immediately prior to the administration of vitamin D). These samples were analyzed for 25-hydroxycholecalciferol (25-OH-$D_3$) and 1,25-$(OH)_2D_3$ using established methods.

Data are expressed as the means±standard deviation of the mean. Statistical significance was determined by a comparison of proportions and Student's two-tailed t-test using 95% confidence intervals.

Preliminary analysis of the data showed no differences between values obtained from vitamin D-replete animals fed the vitamin D-deficient diet with vitamin D supplementation by intraperitoneal injection and the vitamin D-replete animals fed the standard laboratory rodent ration. All data for vitamin D-replete males and females from both diet groups were combined for subsequent analysis and presentation.

The concentrations of Ca and $P_i$ in the serum of vitamin D-replete and vitamin D-deficient animals are given in Table 3. Group 1 vitamin D-deficient females had a significantly lower serum concentration of Ca (4.7±0.3 mg/100 ml) than vitamin D-replete females (9.5 ±0.4 mg/100 ml) prior to their first mating. Serum $P_i$ concentrations were significantly higher in Group 1 vitamin D-deficient females (9.6± 1.8 mg/100 ml) when compared to values in vitamin D-replete females (6.9±0.6 mg/100 ml). Serum Ca concentrations in Group 2 vitamin D-deficient females were not significantly different from vitamin D-replete females prior to mating for the first time, but serum $P_i$ concentrations (1.4±0.2mg/100 ml) were significantly lower than those in vitamin D-replete females (6.9±0.6 mg/100 ml). Group 3 vitamin D-deficient females had a significantly lower serum concentration of calcium (7.3±0.5 mg/100 ml) than vitamin D-replete females prior to mating for the first time. Serum $P_i$ concentrations in Group 3 vitamin D-deficient females were not significantly different from vitamin D-replete females at this time. Serum Ca concentrations in Group 3 vitamin D-deficient females were significantly higher than serum Ca concentrations in Group 1 vitamin D-deficient females.

Post-mating (pre-treatment) vitamin D-deficient females from Group 1 had significantly lower serum Ca concentrations (5.8±0.6 mg/100 ml) than vitamin D-replete females (9.9±0.8 mg/100 ml), but serum $P_i$ was not significantly different at this time. Serum Ca concentrations in Groups 2 and 3 vitamin D-deficient females were not significantly different from vitamin D-replete females at this time. Serum $P_i$ concentrations from Group 2 vitamin D-deficient females (3.3±1.5 mg/100 ml) and Group 3 vitamin D-deficient females (5.2±2.3 mg/100 ml) were significantly lower than values from vitamin D-replete females (8.6±1.0) after their first mating.

For Group 1 vitamin D-deficient female rats that received vitamin $D_3$ or 1,25-$(OH)_2D_3$ treatment, serum concentrations of Ca and $P_i$ were not different from vitamin D-replete female rats.

Concentrations of serum vitamin D metabolites are given in Table 4. Serum from vitamin D-replete females contained 12±2 ng/ml of 25-OH-$D_3$ and 54±14 pg/ml of 1,25-$(OH)_2D_3$. Serum from Group 1 vitamin D-deficient females contained nondetectable levels of 25-OH-$D_3$ and 10±4 pg/ml of 1,25-$(OH)_2D_3$. Serum concentrations of 25-OH-$D_3$ and 1,25-$(OH)_2D_3$ were nondetectable in Groups 2 and 3 vitamin D-deficient females. With respect to 25-OH-$D_3$, these results verify that the animals fed the vitamin D-deficient diet were, in fact, vitamin D deficient. However, because of the finite detectability limits for the 1,25-$(OH)_2D_3$ assay (lower limit of detectability is 10 pg/ml), it is impossible to say that these animals were absolutely vitamin D deficient.

The overall effect of vitamin D deficiency in female rats on mating and fertility is summarized in Table 5. To quantitate fertility, two ratios as defined earlier in Example I were used, i.e. the mating ratio and the fertility ratio. The mating ratio attempts to measure the likelihood of a successful mating and assuming an estrous cycle of 4-5 days, the theoretical value should be 0.20-0.25. From Table 5, the observed value for the mating ratio in the vitamin D-replete animals was 0.20, in agreement with the theoretical value. In Group 1 vitamin D-deficient females, the mating ratio was 0.14, implying that the likelihood of a successful mating in this group of vitamin D-deficient females was approximately 70% that of females in the vitamin D-replete state. For Group 2 vitamin D-deficient females, the mating ratio was 0.08, indicating that the likelihood of a successful mating in this group of vitamin D-deficient females was approximately 40% that of females in the vitamin D-replete state. The mating ratio in Group 3 vitamin D-deficient females was 0.11, indicating the likelihood of a successful mating in this group of vitamin D-deficient females was 55% that of females in the vitamin D-replete state.

The fertility ratio provides a means of quantitating the likelihood of a successful mating and pregnancy. The fertility ratio would equal the mating ratio if every mating resulted in the delivery of a normal, healthy litter. For matings with vitamin D-replete females (Table 5), the fertility ratio was slightly less than the mating ratio, indicating that there were a number of abnormal pregnancies and deliveries. In the matings from Group 1 vitamin D-deficient females, the fertility ratio was 0.05. This was significantly less than the mating ratio of 0.15 from vitamin D-replete females and indicates that the likelihood of this group of vitamin D-deficient females giving rise to a pregnancy resulting in a normal, healthy litter was approximately 33% of that observed in litters from vitamin D-replete females. In Group 2 vitamin D-deficient females, there were no normal, healthy litters, indicating that this group of vitamin D-deficient females giving rise to a normal, healthy litter was unlikely. For Group 3 vitamin D-deficient females, the fertility ratio was 0.02. This was significantly less than the fertility ratio of 0.15 from vitamin D-replete females and indicates that the likelihood of this group of vitamin D-deficient females giving rise to a pregnancy resulting in a normal, healthy litter was approximately 13% of that observed in the vitamin D-replete females. These results show that the overall fertility was reduced 67-100% when females were vitamin D deficient, regardless of the dietary calcium content or serum calcium concentration.

The effect of female vitamin D deficiency on litter size is shown in Table 5. In the vitamin D-replete females, the mean number of pups per litter was 12.6±3.3. In Group 1 vitamin D-deficient females, the mean litter size was 8.2±3.0 and in Group 3 vitamin D-deficient females the mean litter size was 7.9 ±4.0. Group 2 vitamin D-deficient females gave birth to no normal, healthy litters. All vitamin D-deficient female litter sizes were significantly smaller than litter sizes from vitamin D-replete females.

The effect of vitamin D treatment on mating and fertility in Group 1 vitamin D-deficient female rats is summarized in Table 6. For matings of vitamin D-replete female rats, the mating ratio was 0.20 in agreement with the theoretical value of 0.20-0.25. For vitamin D-deficient females that received vitamin $D_3$ the mating ratio was 0.24 and for vitamin D-deficient females that received 1,25-$(OH)_2D_3$, the mating ratio was 0.17, both showing no significant difference from vitamin D-replete female rats. The fertility ratio from vitamin D-deficient females that vitamin $D_3$ was 0.09 and from vitamin D-deficient females that received 1,25-$(OH)_2D_3$ the fertility ratio was 0.04, both of which were not significantly different from the fertility ratio of 0.11 from vitamin D-replete females. The fertility ratio of 0.11 in vitamin D-replete male rats was not different from the fertility ratio of 0.15 from the same animals when mated for the first time (Table 5). There were no significant differences in the percentage of pregnant animals giving birth to normal, healthy litters and the mean litter sizes between vitamin D-replete females and the vitamin D-deficient females that received vitamin D treatment.

As a result, it is concluded that although vitamin D-deficient female rats can reproduce, an examination of their reproductive capacity has shown that the absence of vitamin D reduces their mating success and fertility as compared with vitamin D-replete female rats. The experiments reported in this Example demonstrate that vitamin D deficiency in female rats reduces fertility and reproductive capacity regardless of serum Ca concentration. This Example also shows that vitamin $D_3$ and 1,25-$(OH)_2D_3$ can restore these reproductive functions in vitamin D-deficient animals.

The serum concentration of 1,25-$(OH)_2D_3$ in Group 1 vitamin D-deficient females was found to be 10 ±4 pg/ml, suggesting that these animals were not absolutely vitamin D deficient. Although significantly lower than serum concentrations of 1,25-$(OH)_2D_3$ in vitamin D-replete animals, these values test the limits of detectability of the 1,25-$(OH)_2D_3$ assay, making it impossible to say that these animals were absolutely vitamin D deficient. It is possible, however, that the levels of 1,25-$(OH)_2D_3$ found in vitamin D-deficient animals represent a contamination by vitamin D from external sources. At the time blood was drawn for serum vitamin D determinations, serum calcium concentrations in vitamin D-deficient females had risen significantly to 5.8±0.6 mg/100 ml from 4.7±0.3 mg/100 ml prior to mating. Since vitamin D-deficient females were housed in the same cages with vitamin D-replete males for up to 10 days while mating, there was the possibility of transfer of vitamin D (e.g. coprophagy, grooming). However, with serum concentrations of 1,25-$(OH)_2D_3$ on the order of 10±4 pg/ml, non-detectable levels of serum 25-OH-$D_3$ and serum calcium concentrations on the order of 4.7 mg/100 ml, it was apparent these animals were, in fact, vitamin D deficient.

The probability of a female becoming pregnant (sperm-positive smear) in the vitamin D-deficient state in a given time period was approximately 70% in Group 1, 45% in Group 2 and 55% in Group 3 vitamin D-deficient females, when compared to sperm-positive smears in the vitamin D-replete female rats. The reason for this was not apparent but analysis of the daily vaginal smears taken showed vitamin D-replete females were cycling in the normal 4-5 day period, while vitamin D-deficient females were not cycling in the normal 4-5 day period.

This Example showed that vitamin D-deficient female rats can reproduce, but the absence of vitamin D reduced reproductive capacity and fertility in female rats. This Example also demonstrated that mating success and fertility are adversely affected by vitamin D deficiency in female rates regardless of serum Ca concentrations. Group 2 vitamin D-deficient females were normocalcemic but hypophosphatemic throughout the mating experiment. These animals were clearly rachitic and their small size may have contributed to their reproductive failure. Group 3 vitamin D-deficient females were maintained normocalcemic and normophosphatemic, without being rachitic, and were comparable in size and mating activity with Group 1 vitamin D-deficient females. However, Group 3 females could not support normal reproductive functions. These results clearly show that vitamin D deficiency with normocalcemia impaired mating success and fertility, implying that vitamin D deviciency per se and not hypocalcemia was directly responsible.

The results showed that fertility was reduced approximately 67% in Group 1, 100% in Group 2, and 84% in Group 3 vitamin D-deficient females when compared to vitamin D-replete females. A reduced probability of a successful mating and an increased probability of complications during pregnancy and parturition was associated with reduced fertility. The probability of vitamin D-deficient females rearing normal, healthy litters was 33% for Group 1, 16% for Group 2 and 0% for Group 3, of the total number of pregnancies. This was significantly different from pregnancies by vitamin D-replete females which gave birth to normal, healthy litters in 76% of their pregnancies. The reason for this difference is primarily due to the development of a greater number of complications during pregnancy that resulted in abnormal litters. In those vitamin D-deficient females maintaining a successful pregnancy, gestation and parturition were similar to those observed in vitamin D-replete females. However, litter sizes were clearly reduced.

It has been suggested that the reduction in fertility and litter size in vitamin D-deficient female rats may not be directly influenced by vitamin D deficiency, but rather a result of the fact that vitamin D-deficient females were smaller in size. However, evidence to support a direct vitamin D effect on reproduction and fertility and the likelihood of a normal, healthy litter is the fact that vitamin D treatment restored the percent of pregnancies terminating with normal, healthy litters and litter sizes that were not significantly different from vitamin D-replete females.

TABLE 1

Concentrations of Ca and $P_i$ in serum from vitamin D-replete and vitamin D-deficient rats.

| Group | Ca mg/100 ml* | $P_i$ mg/100 ml* |
|---|---|---|
| Premating | | |
| Vitamin D-deficient males | 5.1 ± 0.5 (9) | 8.7 ± 1.5 (7) |
| Vitamin D-replete males | 9.9 ± 0.5 (8) | 8.6 ± 1.9 (6) |
| Vitamin D-replete females | 9.5 ± 0.4 (7) | 6.9 ± 0.6 (6) |
| Post-Mating/Pre-Replacement Therapy | | |
| Vitamin D-deficient males | 7.1 ± 0.6 (10) + | 8.2 ± 0.6 (3) |
| Vitamin D-replete males | 10.0 ± 0.2 (9) | 8.5 ± 1.3 (8) |
| Vitamin D-replete females | 9.9 ± 0.8 (9) | 8.4 ± 0.9 (6) |
| Post-Replicant Therapy | | |
| Vitamin D-deficient, $D_3$ replacement | 10.6 ± 0.8 (3) | 6.7 ± 1.3 (3) |
| Vitamin D-deficient, 1,25 replacement | 11.0 ± 0.8 (3) | 8.0 ± 0.6 (3) |
| Vitamin D-replete males | 9.9 ± 0.1 (3) | 7.2 ± 0.6 (3) |
| Vitamin D-replete females | 10.0 ± 0.2 (3) | 7.2 ± 0.8 (3) |

*Values given are mean ± standard deviation; the number in parentheses are number of animals analyzed.
p < 0.01 when compared to vitamin D-replete animals.
+p < 0.01 when compared to vitamin D-deficient males prior to mating.

TABLE 2

Effects of vitamin D deficiency in male rats on mating and fertility.

| | Pre-Treatment | | Post-Treatment | | |
|---|---|---|---|---|---|
| | Vitamin D Replete | Vitamin D Deficient | Vitamin D Replete | Vitamin D Deficient | |
| | | | | vitamin $D_3$[A] | 1,25-$(OH)_2D_3$[B] |
| Number of animals mated (males/females)[C] | 40/49 | 66/85 | 15/19 | 17/25 | 17/24 |
| Total animal days mated[C] | 212 | 499 | 74 | 93 | 109 |
| Number of animals becoming pregnant[D] | 42 | 55 | 15 | 22 | 24 |
| Mating ratio[E] | 0.20 | 0.11[G] | 0.20 | 0.24 | 0.22 |
| Fertility ratio[F] | 0.15 | 0.04[G] | 0.11 | 0.12 | 0.07 |
| % pregnant animals giving birth to normal litters | 76 | 40[a] | 53 | 50 | 34 |
| Mean litter size | 12.6 ± 3.3 | 10.4 ± 2.0 | 12.6 ± 4.3 | 10.7 ± 4.5 | 10.4 ± 3.5 |

TABLE 2-continued

Effects of vitamin D deficiency in male rats on mating and fertility.

|  | Pre-Treatment | | Post-Treatment | | |
|---|---|---|---|---|---|
|  | Vitamin D Replete | Vitamin D Deficient | Vitamin D Replete | Vitamin D Deficient | |
|  |  |  |  | vitamin $D_3$[A] | 1,25-$(OH)_2D_3$[B] |
| % active males[H] | 90 | 73[I] | 87 | 94 | 100 |

[A] Vitamin D-deficient males that received $D_3$ (cholecalciferol) treatment.
[B] Vitamin D-deficient males that received 1,25-$(OH)_2D_3$ treatment.
[C] Total animal days mated = animals times number of days mated.
[D] Sperm-positive smears.
[E] Mating ratio = number of pregnant animals divided by total animals days mated.
[F] Fertility ratio = number of pregnant animals giving birth to normal, healthy litters divided by total animal days mated.
[G] $p < 0.01$ when compared to vitamin D-replete males.
[H] Percent of total males mated that successfully inseminated females.
[I] $p < 0.05$ when compared to vitamin D-replete males.

TABLE 3

Concentrations of Ca and $P_i$ in serum from vitamin D-deficient and vitamin D-replete rats.

| Group | Ca | $P_i$ |
|---|---|---|
|  | mg/100 ml* | |
| Pre-mating | | |
| Vitamin D-deficient females Group 1 | 4.7 ± 0.3 (8) | 9.6 ± 1.8 (3) |
| Vitamin D-deficient females Group 2 | 10.0 ± 0.3 (6) | 1.4 ± 0.2 (3) |
| Vitamin D-deficient females Group 3 | 7.3 ± 0.5 (3) + | 7.4 ± 0.7 (3) |
| Vitamin D-replete females | 9.5 ± 0.4 (8) | 6.9 ± 0.06 (6) |
| Vitamin D-replete males | 9.9 ± 0.5 (8) | 8.6 ± 1.9 (6) |
| Post-mating/Pre-replacement | | |
| Vitamin D-deficient females Group 1 | 5.8 ± 0.6 (7) + | 7.6 ± 1.7 (6) |
| Vitamin D-deficient females Group 2 | 9.7 ± 0.4 (5) | 3.3 ± 1.5 (3) |
| Vitamin D-deficient females Group 3 | 9.4 ± 0.7 (6) | 5.2 ± 2.3 (3) |
| Vitamin D-replete females | 9.9 ± 0.8 (9) | 8.6 ± 1.0 (7) |
| Vitamin D-replete males | 10.0 ± 0.2 (9) | 8.5 ± 1.3 (8) |
| Post-replacement | | |
| Vitamin D-deficient females, $D_3$ replacement | 9.6 ± 0.1 (3) | 7.2 ± 0.2 (3) |
| Vitamin D-deficient females, 1,25-replacement | 10.7 ± 0.5 (3) | 7.1 ± 0.5 (3) |
| Vitamin D-replete females | 9.9 ± 0.1 (3) | 7.6 ± 0.6 (3) |
| Vitamin D-replete males | 10.0 ± 0.2 (3) | 7.2 ± 0.8 (3) |

*Values given are mean ± standard deviation; the number in parentheses are number of animals analyzed.
$p < 0.01$ when compared to vitamin D-replete females.
+$p < 0.01$ when compared to pre-mating Group 1 vitamin D-deficient females.

TABLE 4

Serum concentrations of 25-OH-$D_3$ and 1,25-$(OH)_2D_3$ in vitamin D-deficient and vitamin D-replete rats.

| Group | 25-OH-$D_3$ ng/ml* | 1,25-$(OH)_2D_3$ pg/ml |
|---|---|---|
| Vitamin D-deficient females Group 1 (5)+ | ND | 10 ± 4++ |
| Vitamin D-deficient females Groups 2 and 3 (4) | ND | ND |
| Vitamin D-replete females (5) | 12 ± 2 | 54 ± 14 |
| Vitamin D-replete males (4) | 9 ± 2 | 29 ± 8 |

*Values given are mean ± standard deviation.
+Number in parentheses is the number of animals analyzed.
Non-detectable, <5 ng/ml.
Non-detectable, <10 pg/ml.
++$p < 0.01$ when compared to vitamin D-replete animals.

TABLE 5

Effect of vitamin D-deficiency in female rats on mating and fertility.

|  | Vitamin D-replete | Vitamin D-deficient | | |
|---|---|---|---|---|
|  |  | Group 1 | Group 2 | Group 3 |
| Number of animal days mated (Male/Female) | 40/49 | 33/74 | 18/38 | 13/33 |
| Total animal days mated[1] | 212 | 422 | 279 | 221 |
| Number of animals becoming pregnant[2] | 42 | 58 | 22 | 25 |
| Mating ratio[3] | 0.20 | 0.14[a] | 0.08[b] | 0.11[a] |
| Fertility ratio[4] | 0.15 | .05 | 0 | 0.02[b] |
| % pregnant animals giving birth to normal litters | 76 | 33[b] | 0 | 16[b] |

TABLE 5-continued

Effect of vitamin D-deficiency in female rats on mating and fertility.

| | Vitamin D-replete | Vitamin D-deficient | | |
|---|---|---|---|---|
| | | Group 1 | Group 2 | Group 3 |
| Mean litter size | 12.6 ± 3.3 | 8.2 ± 3.0$^b$ | 1$^c$ | 7.9 ± 4.0$^b$ |

[1] Total animal days = Σanimals times number of days mated.
[2] Sperm-positive smears.
[3] Mating ratio = number of animals being pregnant divided by total animal days.
[4] Fertility ratio = number of pregnant animals giving birth to normal litters divided by total animal days mated.
$^a$ p < 0.05 when compared to vitamin D-replete females.
$^b$ p < 0.01 when compared to vitamin D-replete females.
$^c$ One female gave birth to one dead pup.

TABLE 6

Effect of vitamin D treatment on mating and fertility in vitamin D-deficient female rats.

| | Vitamin D-replete | Vitamin D-deficient | |
|---|---|---|---|
| | | vitamin D$_3$* | 1,25-(OH)$_2$D$_3$ |
| Number of animals mated (Males/Females) | 15/19 | 17/34 | 16/32 |
| Total animal days mated+ | 74 | 136 | 164 |
| Number of animal becoming pregnant+ | 15 | 32 | 28 |
| Mating ratio+ | 0.20 | 0.24 | 0.17 |
| Fertility ratio+ | 0.11 | 0.09 | 0.04 |
| % pregnant animals giving birth to normal healthy litters | 53 | 38 | 25 |
| Mean litter size | 12.6 ± 4.3 | 10.3 ± 4.1 | 10.1 ± 3.6 |

*Vitamin D-deficient females that received vitamin D$_3$ replacement therapy.
 Vitamin D-deficient females that received 1,25-(OH)$_2$D$_3$ replacement therapy.
+See Table 5.

Various modes of carrying out the invention are contemplated being within the of the following claims particularly pointing out and distinctly claiming the subject matter regarded as the invention.

We claim:

1. A method for improving reproductive functions in a mammal demonstrating diminished reproductive function, said diminished reproductive function being responsive to vitamin D, which comprises administering to said mammal an amount of a vitamin D compound sufficient to improve fertility and reproductive capacity of said mammal.

2. The method of claim 1 wherein said vitamin D compound is selected from the group consisting of vitamin D$_3$, vitamin D$_2$, 1α-hydroxyvitamin D$_3$, 1α-hydroxyvitamin D$_2$, 1α-25-dihydroxyvitamin D$_3$, 1α, 25-dihydroxyvitamin D$_2$, 25-dihydroxyvitamin D$_3$, 1α,25-dihydroxyvitamin D$_2$, 25-hydroxyvitamin D$_3$, 25-hydroxyvitamin D$_2$, 24,24-difluoro-25-hydroxyvitamin D$_3$, 24,24-difluoro-1α, 25-dihydroxyvitamin D$_3$, 24-fluoro-25-hydroxyvitamin D$_3$, 24-fluoro-1α,25-dihydroxyvitamin D$_3$, 2β-fluoro-25-hydroxyvitamin D$_3$, 2β-fluoro-1-hydroxy-vitamin D$_2$, 2β-fluoro-1α,25-dihydroxyvitamin D$_3$, 26,26,26,27,27,27-hexafluoro-25-hydroxyvitamin D$_3$, 26,26,26,27,27,27-hexafluoro-1α,25-dihydroxyvitamin D$_3$, 24,25-dihydroxyvitamin D$_3$, 1α,24,25-trihydroxyvitamin D$_3$, 25,26-dihydroxyvitaminD$_3$, 1α,25,26-trihydroxyvitamin D$_3$, 23,25-dihydroxyvitamin D$_3$, 23,25,26-trihydroxyvitamin D$_3$, and the corresponding 1α-hydroxylated forms, 25-hydroxyvitamin D$_3$-26,23-lactone and its 1α-hydroxylated derivative, the side chain nor, dinor, trinor and tetranor-analogs of 25-hydroxyvitamin D$_3$ and of 1α, 25-dihydroxyvitamin D$_3$, 1α-hydroxypregnacalciferol, and its homo and dihomo derivatives, 1α,25-dihydroxy-24-epi-vitamin D$_2$, 24-homo-1,25-dihydroxyvitamin D$_3$, 24-trihomo-1,25-dihydroxyvitamin D$_3$ and the corresponding 26- or 26,27-homo, dihomo or trihomo analogs of 1α,25-dihydroxyvitamin D$_3$.

3. The method of claim 1 wherein the vitamin D compound is administered in an amount of from about 0.1 micrograms to about 2 milligrams per day.

4. The method of claim 1 wherein said vitamin D compound is administered daily to said mammal for about 1 week to about 8 months.

5. The method of claim 1 wherein said vitamin D compound is administered orally in a liquid vehicle ingestible by and non-toxic to said mammal.

6. The method of claim 1 wherein said vitamin D compound is combined with a non-toxic pharmaceutically acceptable carrier prior to administration.

7. The method of claim 1 wherein the compound used is vitamin D$_3$.

8. The method of claim 1 wherein the compound used is 1,15-dihydroxyvitamin D$_3$.

9. A method of improving reproductive functions in a mammal demonstrating diminished reproductive function, said diminished reproductive function being responsive to vitamin D, which comprises the steps of:
determining whether said mammal has a vitamin D deficiency; and
administering to said mammal an amount of a vitamin D compound sufficient to improve fertility and reproductive capacity of said mammal.

10. The method of claim 9 wherein said vitamin D compound is selected from the group consisting of vitamin D$_3$, vitamin D$_2$, 1α-hydroxyvitamin D$_3$, 1α-hydroxyvitamin D$_2$1α,25-dihydroxyvitamin D$_3$, 1α,25-dihydroxyvitamin D$_2$, 25-hydroxyvitamin D$_3$,25-hydroxyvitamin D$_2$, 24,24-difluoro-25-hydroxyvitamin D$_3$, 24,24-difluoro-1α, 25-dihydroxyvitamin D$_3$, 24-fluoro-25-hydroxyvitamin D$_3$, 24-fluoro-1α, 25-dihydroxyvitamin D$_3$, 2β-fluoro-25-hydroxyvitamin D$_3$, 2β-fluoro-1α-hydroxyvitamin D$_2$, 2β-fluoro-1α,25- dihydroxyvitamin $D_3$, 26,26,26,27,27,27-hexafluoro-25-hydroxyvitamin $D_3$, 26,26,26,27,27,27-hexafluoro-1α, 25-dihydroxyvitamin $D_3$, 24,25-dihydroxyvitamin $D_3$, 1α, 24,25-trihydroxyvitamin $D_3$, 25,26-dihydroxyvitamin$D_3$, 1α, 25,26-trihydroxyvitamin $D_3$, 23,25-dihydroxyvitamin $D_3$, 23,25,26-trihydroxyvitamin $D_3$, and the corresponding 1α -hydroxylated forms, 25-hydroxyvitamin $D_3$-26,23-lactone and its 1α-hydroxylated derivative, the side chain nor, dinor, trinor and tetranor-analogs of 25-hydroxyvitamin $D_3$ and of 1α,25-dihydroxyvitamin $D_3$, 1α -hydroxypregnacalciferol, and its homo and dihomo derivatives, 1α25-dihydroxy-24-epi-vitamin $D_2$, 24-homo-1,15-dihydroxyvitamin $D_3$ 24-dihomo-1,25-dihydroxyvitamin $D_3$, 24-trihomo-1,25-dihydroxyvitamin $D_3$ and the corresponding 26- or 26,27-homo, dihomo or trihomo analogs of 1α,25-dihydroxyvitamin $D_3$.

11. The method of claim 9 wherein the vitamin D compound is administered in an amount of from about 0.1 micrograms to about 2 milligrams per day.

12. The method of claim 9 wherein said vitamin D compound is administered daily to said mammal for about 1 week to about 8 months.

13. The method of claim 9 wherein said vitamin D compound is administered orally in a liquid vehicle ingestible by and non-toxic to said mammal.

14. The method of claim 9 wherein said vitamin D compound is combined with a non-toxic pharmaceutically acceptable carrier prior to administration.

15. The method of claim 9 wherein the compound used is vitamin $D_3$.

16. The method of claim 9 wherein the compound used is 1,25-dihydroxyvitamin $D_3$.

* * * * *

UNITED STATES PATENT AND TRADEMARK OFFICE
CERTIFICATE OF CORRECTION

PATENT NO. : 4,970,203
DATED : November 13, 1990
INVENTOR(S) : Hector F. DeLuca et al It is certified that error appears in the above-identified patent and that said Letters Patent is hereby corrected as shown below:

Claim 2, Col. 15, Line 47, after first occurrence of "1α" delete "-"and substitute therefore --- , ---; Claim 2, Col. 15, Lines 48-49, delete "25-dihydroxyvitamin $D_3$, 1α,25-dihydroxyvitamin $D_2$";

Claim 2, Col. 15, Line 68, delete "trihomo" and substitute therefore --- dihomo ---; Claim 2, Col. 15, Line 68, after "$D_3$" insert --- , 24-trihomo-1, 25-dihydroxyvitamin $D_3$---; Claim 8, Col. 16, Line 49, change "15" to --- 25 ---; Claim 10, Col. 16, Line 62, after "$D_2$" insert --- , ---; Claim 10, Col. 17, Line 12, after "1α" insert --- ,---; Claim 10, Col. 17, Line 13, change "15" to --- 25 ---; Claim 10, Col. 17, Line 14, after the first occurrence of "$D_3$" insert --- , ---.

Signed and Sealed this

Twenty-second Day of September, 1992

*Attest:*

DOUGLAS B. COMER

*Attesting Officer*    *Acting Commissioner of Patents and Trademarks*

UNITED STATES PATENT AND TRADEMARK OFFICE
CERTIFICATE OF CORRECTION

PATENT NO. : 4,970,203
DATED : November 13, 1990
INVENTOR(S) : Hector F. DeLuca, et al It is certified that error appears in the above-indentified patent and that said Letters Patent is hereby corrected as shown below:

Column 1, line 6, insert the following paragraph:

--- This invention was made with United States Government support awarded by the National Institute of Health (NIH), Grant No. DK-14481. The United States Government has certain rights in this invention. ---

Signed and Sealed this

Fourteenth Day of December, 1993

Attest:

BRUCE LEHMAN

*Attesting Officer*      *Commissioner of Patents and Trademarks*